US005637582A

United States Patent [19]

Murata et al.

[11] Patent Number: 5,637,582

[45] Date of Patent: Jun. 10, 1997

[54] PERIPHERAL CIRCULATION IMPROVING AGENT

[75] Inventors: Sakae Murata, Kawagoe; Hiroshi Narita, Urawa; Minako Kaburaki, Toda, all of Japan

[73] Assignee: Tanabe Seiyaku Co., Ltd., Osaka, Japan

[21] Appl. No.: 447,228

[22] Filed: May 22, 1995

Related U.S. Application Data

[63] Continuation-in-part of Ser. No. 408,001, Mar. 21, 1995, abandoned, which is a continuation-in-part of Ser. No. 137,514, Oct. 18, 1993, abandoned.

[30] Foreign Application Priority Data

Oct. 23, 1992 [JP] Japan .................................. 4-284834

[51] Int. Cl.$^6$ .................................................. A61K 31/55

[52] U.S. Cl. ............................................................ 514/211

[58] Field of Search .............................................. 514/211

[56] References Cited

U.S. PATENT DOCUMENTS 3,562,257 2/1971 Kugita ................................ 260/239.3

FOREIGN PATENT DOCUMENTS

| | | |
|---|---|---|
| 1291134 | 10/1991 | Canada . |
| 0154838 | 9/1985 | European Pat. Off. . |
| 0158340 | 10/1985 | European Pat. Off. . |
| 0318398 | 5/1989 | European Pat. Off. . |
| 0476854 | 3/1992 | European Pat. Off. . |
| 0555042 | 8/1993 | European Pat. Off. . |
| 2626000 | 7/1989 | France . |
| 1227852 | 1/1989 | Italy . |
| 53-18038 | 9/1988 | Japan . |

OTHER PUBLICATIONS

Kanazawa et al, J. Cardiovascular Pharmacol., 16 (3), pp. 430–437, 1990.

Remington's Pharmaceutical Sciences, 16th edition, 198, p. 420, 1980.

Week 8411, Derwent Publications Ltd., London, GB; AN 84–065035 & JP-A-59 020 221 (Tanabe Seiyaku Co., Ltd.), 1984.

Niceritrol, Pharmacological Studies on Niceritrol (10), The Effects on Experimental Models of Peripherally Circulatory Insufficiency, pp. 859–866, 1982.

S. Nishio et al. Effect of Beraprost Sodium on Peripheral Circulatory Disturbances Induced by Various Stimuli Arzneim.–Forsch./Drug Res. 39 (II), Nr. 10 (1989).

Derek J. Trezise et al. Cromakalim does not protect against skeletal muscle fatigue in an anasthetized rat model of acute hindlimb ischaemia, European Journal of Pharmacology, 250 (1993) pp. 109–116.

*Primary Examiner*—Phyllis G. Spivack
*Attorney, Agent, or Firm*—Browdy and Neimark

[57] ABSTRACT

There is disclosed (−)-cis-1,5-benzothiazepine represented by the following formula or pharmaceutically acceptable salt thereof:

(I)

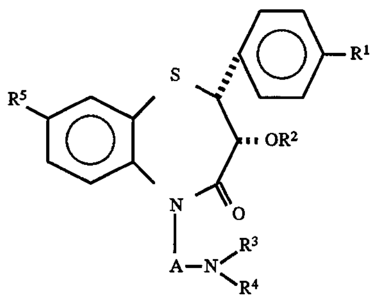

wherein $R^1$ represents lower alkyl or lower alkoxy; $R^2$ represents hydrogen or lower alkanoyl; $R^3$ represents lower alkyl; $R^4$ represents hydrogen or lower alkyl; $R^5$ represent hydrogen, lower alkyl or hydroxy lower alkyl; and A represents lower alkylene, which is a prophylactic and/or curing agent of Raynaud's disease and chronic arterial obstruction.

11 Claims, No Drawings

PERIPHERAL CIRCULATION IMPROVING AGENT

CROSS-REFERENCE TO RELATED APPLICATIONS

This is a continuation-in-part application of Ser. No. 08/408,001, filed Mar. 21, 1995, now abandoned, which is a continuation-in-part application of Ser. No. 08/137,514, filed on Oct. 18, 1993, now abandoned, the entire contents of both of which are hereby incorporated by reference.

BACKGROUND OF THE INVENTION

1. Field of the invention

The present invention relates to a peripheral circulation improving agent. More particularly, the present invention relates to a peripheral circulation improving agent which has improved activity on peripheral circulation and is useful as a therapeutic and/or prophylactic agent of Raynaud's disease, chronic arterial obstruction (e.g., arteriosclerosis obliterans and Buerger's disease) and the like.

2. Discussion of the Background

It has been known that 1,5-benzothiazepine derivatives such as 2-(4-lower alkylphenyl)-3-lower alkanoyloxy (or hydroxy)-5-(2-di-lower alkylaminoethyl)-8-lower alkyl-2,3-dihydro-1,5-benzothiazepin-4(5H)-one and 2-(4-lower alkylphenyl)-3-lower alkanoyloxy (or hydroxy)-5-(2-mono-lower alkylaminoethyl)- 8-lower alkyl-2,3-dihydro-1,5-benzothiazepin-4(5H)-one have antihypertensive, cerebral and coronary vasodilating and/or platelet aggregation-inhibiting activities (for example, EP-A-0 154 838 and EP-A-0 158 340).

It has also been known that a pharmaceutical composition of acetylsalicylic acid and the above-mentioned benzothiazepine derivatives has excellent inhibitory effects on the platelet aggregation (EP-A-0 476 854).

SUMMARY OF THE INVENTION

The present invention has been accomplished by finding the fact that a (–)-cis-1,5-benzothiazepine derivative of the present invention shows, as a sole active ingredient, specific femoral arterial blood flow increasing activity, showing substantially no effect on vertebral arterial blood flow or blood pressure. From a consideration of the prior art, one skilled in the art would have expected that a 1,5-benzothiazepine derivative would affect various cardiovascular systems, such as by having hypotensive activity and coronary vasodilating activity. That the compounds of the present invention have properties which eliminate such side effects, was totally unpredictable and unexpected and, thus, makes this an unexpectedly superior compound for the prophylaxis or treatment of conditions responsive to improved peripheral circulation.

Thus, the present invention relates to a method for prophylaxis or treatment of conditions responsive to improved peripheral circulation in a warm-blooded animal, comprising the steps of administering to said warm-blooded animal a (–)-cis-1,5-benzothiazepine derivative, represented by the following formula:

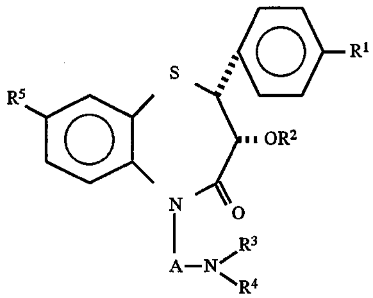

(I)

wherein $R^1$ represents a lower alkyl group or a lower alkoxy group; $R^2$ represents hydrogen atom or a lower alkanoyl group; $R^3$ represents a lower alkyl group; $R^4$ represents hydrogen atom or a lower alkyl group; $R^5$ represents hydrogen atom, a lower alkyl group or a hydroxy lower alkyl group; and A represents a lower alkylene group, or a pharmaceutically acceptable salt thereof, as a sole active ingredient, at an amount which is effective for ameliorating conditions responsive to improved peripheral circulation, but shows substantially no effect on vertebral arterial blood flow or blood pressure.

DESCRIPTION OF THE PREFERRED EMBODIMENT

A (–)-cis-1,5-benzothiazepine derivative according to formula (I) or a pharmaceutically acceptable salt thereof, as the only active ingredient of the present invention has an outstanding advantage in that it exhibits a highly increased activity on peripheral circulation, i.e., it remarkably increases femoral arterial blood flow, and that the increased circulation activity continues for a long period of time.

Furthermore, a (–)-cis-1,5-benzothiazepine derivative according to formula (I) has low toxicity and can be used safely. For example, the herein described test compound A was orally given to a mouse in a dosage of 1000 mg/kg, no lethal toxicity was observed even after 2 days.

Accordingly, a (–)-cis-1,5-benzothiazepine derivative of formula (I), or a pharmaceutically acceptable salt thereof, of the present invention is useful as a peripheral circulation improving agent. As such it can be used for the prophylaxis or treatment of any condition in a warm blooded animal which responds to improved peripheral circulation. The term "conditions responsive to improved peripheral circulation" is intended to include any such condition, including peripheral circulation disorders and peripheral circulation insufficiency diseases. More specifically, this term is intended to include the treatment and/or prophylaxis of Raynaud's disease, chronic arterial obstruction (e.g., arteriosclerosis obliterans and Buerger's disease) and the like in warm-blooded animals including human beings.

For example, as clearly seen from Experimental example 4 mentioned hereinbelow, (–)-cis form test compounds A and F showed excellent femoral arterial blood flow increasing activity even after 30 minutes intravenously injected to dogs under anesthesia in an amount of 100 μg/kg and exerted substantially no effect on vertebral arterial blood flow and arterial blood pressure, whereas (+)-cis form test compounds G and H showed remarkable changes in vertebral arterial blood flow and arterial blood pressure one minute after the administration and increase in femoral arterial blood flow substantially disappeared 10 minutes after the administration.

Also, as clearly seen from Experimental example 7 mentioned hereinbelow, in a rat hind leg frostbite model, the test compound A showed edema inhibition activity whereas the commercially available platelet aggregation inhibiting agents, such as ticlopidine and acetyl salicylic acid, did not show any edema inhibition activity.

Further, as clearly seen from the Clinical example mentioned hereinbelow, the test compound A showed effects of "improved" or more in about 25 patients among 40 patients suffering from arteriosclerosis obliterans or Buerger's disease.

As described above, the effectiveness of the present invention in an animal model and/or in clinical test is clear. It is particularly effective in rat hind leg frostbite model which had not been improved by the conventional platelet aggregation inhibiting agents, and also it has the excellent characteristic that substantially no effect is exerted on the heart.

As one non-limiting example of a compound having an excellent therapeutic activity, among the above (−)-cis-1,5-benzothiazepine derivatives of formula (I), there may be mentioned the compound in which $R^1$ is a lower alkyl group, $R^2$ is a lower alkanoyl group, $R^3$ is a lower alkyl group, $R^4$ is a lower alkyl group, and $R^5$ is a lower alkyl group.

According to the present invention, as preferred examples of the lower alkyl group, the lower alkylene group and the lower alkoxy group, there may be mentioned those having 1 to 6 carbon atoms, particularly those having 1 to 4 carbon atoms, more specifically methyl, ethylene and methoxy groups, respectively; and as preferred examples of the lower alkanoyl group, there may be mentioned, without limitation, those having 2 to 6 carbon atoms, particularly those having 2 to 4 carbon atoms, and more specifically an acetyl group.

Other preferred examples of the above (−)-cis-1,5-benzothiazepine derivatives of formula (I), include those in which $R^1$ is methyl group or methoxy group; $R^2$ is hydrogen atom or acetyl group; $R^3$ is methyl group; $R^4$ is hydrogen atom or methyl group; $R^5$ is hydrogen atom, methyl group or hydroxymethyl group; and A is ethylene group.

A (−)-cis-1,5-benzothiazepine derivative of formula (I), as an active ingredient of the present invention can be used for a medical use either in free form or in the form of a pharmaceutically acceptable salt thereof. The pharmaceutically acceptable salt may include, for example, an inorganic acid addition salt such as hydrochloride, hydrobromide, hydroiodide, perchlorate, sulfonate and phosphate; or an organic acid addition salt such as oxalate, maleate, fumarate, tartarate and methanesulfonate.

The dosage of a (−)-cis-1,5-benzothiazepine derivative of formula (I), or a pharmaceutically acceptable salt thereof, may vary depending on the age, the body weight and the health condition of patient, or on the severity of disease, but is about 0.1 to 300 mg/kg per day, preferably 1 to 30 mg/kg per day for oral administration; and about 0.001 to 10 mg/kg per day, preferably 0.01 to 1 mg/kg per day for parenteral administration.

A (−)-cis-1,5-benzothiazepine derivative of formula (I), or a pharmaceutically acceptable salt thereof, can be used by way of either oral administration or parenteral administration.

A (−)-cis-1,5-benzothiazepine derivative of formula (I), or a pharmaceutically acceptable salt thereof, can be orally administered in a dosage form of a solid preparation such as tablets, pills, capsules or powder, or a liquid preparation such as solutions and suspensions, together with a pharmaceutical carrier suitable for oral administration as a pharmaceutical preparation. Such a carrier may include, for example, conventional binders (e.g. syrup, gum arabic, gelatin, sorbitol, tragacanth and polyvinylpyrrolidone), excipients (e.g. lactose, sugar, corn starch, potassium phosphate, sorbitol and glycine), lubricants (e.g. magnesium stearate, talc, polyethyleneglycol and silica), disintegrators (e.g. potato starch), or humectants (e.g. sodium lauryl sulfate).

Alternatively, in the case of parenteral administration, the composition may be preferably used as an injection or injection for drip infusion, by using, for example, distilled water for injection, physiological saline and/or glucose aqueous solution.

A (−)-cis-1,5-benzothiazepine derivative of formula (I), as the active component of the present invention, can be prepared according to a conventional method (for example, methods disclosed in U.S. Pat. No. 3,562,257, EP-A-0 154 838, EP-A-0 158 340, and Italian Patent No. 1,227,852).

For example, a derivative according to formula (I) can be prepared by reacting a compound represented by the formula (II):

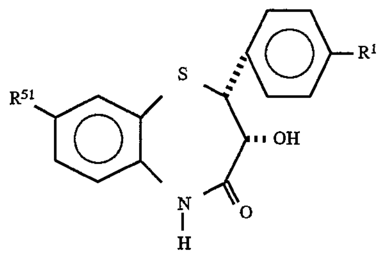
(II)

wherein $R^{51}$ represents hydrogen atom, a lower alkyl group or a hydroxy lower alkyl group having a protective group; and the other symbols have the same meanings as defined above, with a compound represented by the formula (III):

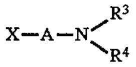
(III)

wherein X represents a halogen atom; and the other symbols have the same meanings as defined above, in the presence of a salt (e.g., an alkali metal salt of carbonic acid), and, if necessary, reacting the resulting compound with an acid anhydride of a compound represented by the formula (IV):

$$R^{21}—OH \quad (IV)$$

wherein $R^{21}$ represents a lower alkanoyl group, in the presence of a deacidifying agent (e.g., an organic amine);

and when $R^{51}$ is a hydroxy lower alkyl group having a protective group, removing said protective group according to a conventional method.

EXAMPLES

Experimental Example 1

(Test Compounds)

The compounds listed in the following Table 1 were used as the test compounds.

TABLE 1

Test Compounds

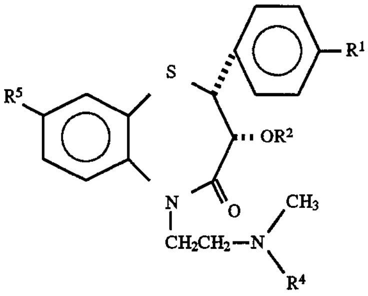

| Test Compound | $R^1$ | $R^2$ | $R^4$ | $R^5$ | Physical properties |
|---|---|---|---|---|---|
| A | $CH_3$ | $COCH_3$ | $CH_3$ | $CH_3$ | Maleate m.p.: 195.0 to 197.5° C. |
| B | $CH_3$ | H | $CH_3$ | $CH_3$ | Hydrochloride m.p.: 138 to 140° C. |
| C | $CH_3$ | $COCH_3$ | H | $CH_3$ | Fumarate m.p.: 167.5 to 170.0° C. |
| D | $CH_3$ | H | H | $CH_3$ | Hydrochloride m.p.: 128 to 145° C. |
| E | $CH_3$ | $COCH_3$ | $CH_3$ | $CH_2OH$ | Oxalate m.p. 168 to 169° C. |
| F | $OCH_3$ | $COCH_3$ | $CH_3$ | H | Hydrochloride m.p.: 206 to 207° C. |

(Method)

Adult dogs (one group consisting of a dog) were intravenously given the test compound under anesthesia and artificial respiration successively at intervals of 60 minutes so that the dose can be 10, 30, 100 and 300 μg/kg body weight, and the blood flow of femoral artery was measured with a time course. The femoral arterial blood flow was measured with an electromagnetic blood flow meter (manufactured by Nihon Koden, MFV-2100, trade name) through a flow probe attached to the femoral artery. An increase in the femoral arterial blood flow was calculated by subtracting the blood flow before the administration of the first dose of test compound as the standard value (the base line) from that 60 minutes after each administration.

(Results)

The increase in the femoral arterial blood flow after the administration of the test compound is shown in Table 2.

TABLE 2

| Test | Increase in femoral arterial blood flow (ml/min) Dosage (μg/kg) | | | |
|---|---|---|---|---|
| Compound | 10 | 30 | 100 | 300 |
| A | 13 | 30 | 34 | 32 |
| B | 22 | 28 | 48 | 74 |
| C | 6 | 19 | 50 | 65 |
| D | — | — | 11 | 35 |
| E | — | 15 | 37 | 36 |
| F | 11 | 21 | 27 | 37 |

Experimental Example 2

(Method)

The test compound A was intravenously administered to adult dogs (one group consisting of 4 dogs) in a dosage of 100 μg/kg body weight and the femoral arterial blood flow was measured at 30, 60, 120, 180, 240 and 300 minutes after the administration in the same manner as in Experimental example 1 to determine an increase in the blood flow based on that before the administration of the test compound.

(Results)

The femoral arterial blood flow and the increase in the blood flow after the administration of the test compound A are shown in Table 3.

TABLE 3

| | Period after administration (min) | | | | | | |
|---|---|---|---|---|---|---|---|
| | Before | 30 | 60 | 120 | 180 | 240 | 300 |
| Blood flow (ml/min) | 80.8 | 136.3 | 146.3 | 143.5 | 141.3 | 141.5 | 136.3 |
| Increase in blood flow (ml/min) | | 55.5 | 65.5 | 62.8 | 60.5 | 60.8 | 55.5 |

Experimental Example 3

(Test Compounds)

The compounds A, B, C, E and F listed in Table 1 were used as the test compounds.

(Method)

Adult dogs (one group consisting of 5 dogs) were intravenously given the test compound under anesthesia and artificial respiration successively at intervals of 60 minutes so that the dose can be 10, 30, 100, 300 and 1000 μg/kg body weight, and the blood flow of femoral artery was measured with a time course. The femoral arterial blood flow was measured with an electromagnetic blood flow meter (manufactured by Nihon Koden, MFV-2100, trade name) through a flow probe attached to the femoral artery. An increase in the femoral arterial blood flow was calculated by subtracting the blood flow before the administration of the first dose of test compound as the standard value (the base line) from that of maximum during an interval of 60 minutes after each administration.

(Results)

The increase in the femoral arterial blood flow after the administration of the test compound is shown in Table 4.

TABLE 4

| Test | Increase in femoral arterial blood flow (ml/min) Dosage (μg/kg) | | | | |
|---|---|---|---|---|---|
| Compound | 10 | 30 | 100 | 300 | 1000 |
| A | 5.6 | 40.4 | 55.2 | 61.4 | |
| B | 10.4 | 16.4 | 41.4 | 70.2 | 79.2 |
| C | — | 6.8 | 25.6 | 44.6 | 49.0 |
| E | — | 15.6 | 55.6 | 69.2 | 68.6 |
| F | 10.7 | 21.0 | 27.3 | 37.0 | |

Experimental Example 4

(Test Compounds)

The compounds A and F listed in Table 1 and the compounds listed in the following Table 5 were used as the test compounds in order to examine the influence caused by the configurational difference between (−)-cis-isomers and (+)-cis-isomers.

TABLE 5

Test Compounds

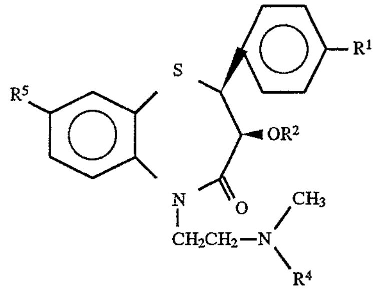

| Test Compound | $R^1$ | $R^2$ | $R^4$ | $R^5$ |
|---|---|---|---|---|
| G | $CH_3$ | $COCH_3$ | $CH_3$ | $CH_3$ |
| H | $OCH_3$ | $COCH_3$ | $CH_3$ | H |

(Method)

Each test compound was intravenously administered to adult dogs (one group consisting of 2 or 4 dogs) under anesthesia and artificial respiration at a dose of 100 μg/kg body weight. Femoral arterial blood flow, vertebral arterial blood flow and arterial blood pressure were measured 1, 3, 5, 10, 20 and 30 minutes after the administration. The femoral arterial blood flow and vertebral arterial blood flow were measured with an electromagnetic blood flowmeter (manufactured by Nihon Koden, MFV-2100, trade name) through a flow probe attached to the femoral artery or vertebral artery. The arterial blood pressure was measured with a pressure transducer (manufactured by Millar, MICRO-TIP, Model SPC-350) through a catheter attached to the brachial artery.

Changes of the femoral arterial blood flow, vertebral arterial blood flow and arterial blood pressure were estimated by comparing the values measured before and after the administration of the test compound.

(Results)

The changes of the femoral arterial blood flow, vertebral arterial blood flow and arterial blood pressure after the administration of each test compound are shown in the following Table 6.

$AUC_{60}$ (Area under the curve for 60 minutes after an administration of a test compound) of the femoral arterial blood flow is shown in the following Table 7.

TABLE 6

(The changes of femoral arterial blood flow, vertebral arterial blood flow and blood pressure)

| | Compound | 1 | 3 | 5 | 10 | 20 | 30 (min) |
|---|---|---|---|---|---|---|---|
| Femoral | F | 10.5 | 36.0 | 48.0 | 63.5 | 64.5 | 54.5 |
| Arterial | A | 3.5 | 5.5 | 7.8 | 13.0 | 21.5 | 28.0 |
| Blood | H | 38.5 | 34.5 | 22.5 | 8.0 | 1.0 | −1.5 |
| Flow (Δ ml/min) | G | 30.0 | 24.0 | 16.0 | 9.5 | 7.5 | 5.0 |
| Side effects | F | −0.5 | −1.0 | −1.0 | 0.0 | 0.0 | 0.5 |
| Vertebral | A | 0.3 | 0.0 | −0.5 | −1.5 | −2.8 | −2.5 |
| Arterial | H | 25.5 | 18.0 | 13.5 | 7.5 | 4.5 | 2.0 |
| Blood | G | 26.5 | 18.0 | 11.5 | 7.0 | 3.5 | 2.5 |
| Flow (Δ ml/min) | | | | | | | |

TABLE 6-continued (The changes of femoral arterial blood flow, vertebral arterial blood flow and blood pressure)

| | Compound | 1 | 3 | 5 | 10 | 20 | 30 (min) |
|---|---|---|---|---|---|---|---|
| Arterial | F | −1.5 | −0.5 | 1.0 | 1.5 | 1.5 | 2.5 |
| Blood | A | −1.3 | −0.8 | −1.8 | −1.8 | −2.3 | −0.5 |
| Pressure | H | −11.5 | −4.5 | −2.0 | −1.0 | 0.0 | 1.0 |
| (ΔmmHg) | G | −11.0 | −2.5 | 1.5 | 1.0 | 1.0 | 1.5 |

TABLE 7

($AUC_{60}$ of the femoral arterial blood flow)

| Compound | $AUC_{60}$ (ml) |
|---|---|
| F | 2977.0 |
| A | 1538.4 |
| H | 300.5 |
| G | 475.3 |

Experimental Example 5

(Lower limbs peripheral circulation disorder model due to hind leg cooling: Model of Raynaud's disease)

(Test Compounds)

The compound A listed in Table 1 was used as the test compound and Beraprost Na (Compound J) was used as a comparative compound.

(Method)

A catheter was inserted into left common carotid artery of a male SD rat (one group consisting of 5 rats) under anesthesia, and the arterial blood pressure was measured with a standard pressure transducer (manufactured by Nihon Koden. TP-200T, trade name) through a catheter attached to the artery. After isolating the left femoral artery from the peripheral connective tissue, a flow probe (HDP 10-20R: F 1.0 mm) of a Doppler blood flow meter (manufactured by Crystal Biotec Co., PD20, trade name) was attached thereto and was connected to the Doppler blood flow meter to measure the artery blood flow. After the operation, at the time that the state became stable, the left hind leg was exposed to a perfused solution at 10° C. to decrease the femoral arterial blood flow. After 30 minutes, 1 ml/kg of a 0.9% NaCl solution or 300 μg/kg of the test compound A was intravenously administered and the state was observed. In the case of Beraprost Na, continuous injection in an amount of 0.3 μg/kg/ml was carried out after 30 minutes from cooling. The compounds to be used were each dissolved in a 0.9% NaCl solution.

The present model is disclosed, for example, in Nishio et al, "Effect of Beraprost Sodium on Peripheral Circulatory Disturbances Induced by Various Stimuli", *Arzneim.-Forsch./Drug Res.*, 39 (II), Nr. 10 (1989), pp. 1229–1234. Note particularly the section "2.4. Sphygmometry in rat hind paw", at page 1230.

(Results)

The changes of the femoral arterial blood flow and arterial blood pressure are shown in the following Table 8.

TABLE 8

| | Compound | 0 | 30 | 40 | 50 | 60 | 70 | 80 | 90 (min) |
|---|---|---|---|---|---|---|---|---|---|
| | | (The changes of the femoral arterial blood flow and arterial blood pressure) | | | | | | | |
| Femoral Arterial Blood Flow (Δ ml/min) | Control | 0.988 ± 0.218 | 0 | 0.008 ± 0.014 | −0.012 ± 0.022 | 0.016 ± 0.037 | −0.004 ± 0.053 | −0.004 ± 0.041 | 0.000 ± 0.044 |
| | A | 1.364 ± 0.319 | 0 | 0.072 ± 0.056 | 0.276 ± 0.092 | 0.416 ± 0.101 | 0.452 ± 0.114 | 0.452 ± 0.154 | 0.496 ± 0.191 |
| | J | 1.116 ± 0.217 | 0 | 0.252 ± 0.077 | 0.304 ± 0.087 | 0.368 ± 0.188 | 0.436 ± 0.283 | 0.372 ± 0.321 | 0.344 ± 0.341 |
| Mean Arterial Blood Pressure (Δ mmHg) | Control | 1.40 ± 2.77 | 0 | 1.40 ± 0.75 | 2.40 ± 1.91 | 3.00 ± 1.92 | 2.22 ± 1.98 | 2.80 ± 1.24 | 3.80 ± 1.59 |
| | A | 0.00 ± 1.22 | 0 | −4.20 ± 1.53 | −4.20 ± 2.18 | −3.80 ± 1.53 | −4.00 ± 2.17 | −4.60 ± 1.69 | −4.20 ± 2.35 |
| | J | 1.20 ± 2.01 | 0 | −11.20 ± 4.27 | −10.60 ± 4.93 | −10.80 ± 4.37 | −11.40 ± 3.72 | −8.80 ± 4.13 | −9.40 ± 4.39 |

Experimental Example 6

(Abdominal aorta knot-anterior tibial muscle contraction model: Model of Buerger's disease)

(Test Compounds)

The compound A listed in Table 1 was used as the test compound.

(Method)

Rats were previously divided into four groups (Group I: sham operation+5 ml/kg/day of distilled water, Group II: sham operation+10 mg/kg/day of the test compound A, Group III: abdominal aorta knot+5 ml/kg/day of distilled water, and Group IV: abdominal aorta knot+10 mg/kg/day of the test compound A), and operated under anesthesia, 10 mg/kg/day of the test compound A or 5 ml/kg/day of distilled water was orally administered to respective rats, to which an abdominal aorta was knotted or a sham operation was applied, for 2 weeks. Thereafter, a catheter was inserted into a trachea to secure airway under anesthesia. A skin at the right hind leg was cut to expose a muscle and a right anterior tibial muscle was isolated. After the operation, at the time that the state became stable, 10 mg/kg of the test compound A or 1 ml/kg of 0.25% CMC was administered into a duodenum. After 60 minutes from the administration, a tendon of the right anterior tibial muscle was connected with a transducer and the right anterior tibial muscle was directly stimulated electrically with platinum electrodes at 0.5 Hz to obtain a Force-Current curve. Then, electrical stimulation was carried out with a current which submaximally contracted the right anterior tibial muscle and a stimulation frequency of 1.5 Hz for 30 minutes to observe the progress.

The present model is disclosed, for example, in Trezise et al, "Cromakalim Does Not Protect Against Skeletal Muscle Fatigue in an Anaesthetized Rat Model of Acute Hindlimb Ischaemia", *Eur. J. of Pharmacol.*, 250: 109–116 (1993), noting particularly the section "2. Materials and Methods", commencing at page 110.

(Results)

The changes in contraction of the right anterior tibial muscle when electrically stimulated with a lapse of time are shown in the following Table 9.

TABLE 9

| Groups | 0 | 1 | 3 | 5 | 10 | 15 | 20 | 30 (min) | Time (min) until 20A% contraction |
|---|---|---|---|---|---|---|---|---|---|
| Group I | 0 | −0.38 ± 1.47 | −1.66 ± 2.35 | −3.96 ± 2.58 | −13.71 ± 1.94 | −20.47 ± 1.65 | −23.71 ± 1.57 | −27.00 ± 2.17 | 16.73 ± 2.17 |
| Group II | 0 | 3.29 ± 1.80 | 1.71 ± 2.88 | −1.29 ± 2.86 | −12.88 ± 3.07 | −20.91 ± 2.83 | −25.66 ± 2.80 | −30.19 ± 3.10 | 16.65 ± 2.99 |
| Group III | 0 | 0.15 ± 1.79 | −8.12 ± 4.01 | −14.57 ± 5.47 | −26.41 ± 5.94 | −33.85 ± 5.57 | −37.43 ± 4.90 | −40.76 ± 3.99 | 9.59 ± 1.46 |
| Group IV | 0 | 2.44 ± 2.33 | −1.04 ± 3.60 | −4.35 ± 4.01 | −15.46 ± 4.43 | −21.82 ± 4.69 | −25.98 ± 4.58 | −30.17 ± 4.35 | 17.27 ± 3.70 |

Experimental Example 7

(Hind leg frostbite model: Model of Raynaud's disease)

(Test Compounds)

The compound A listed in Table 1 was used as the test compound and ticlopidine (Compound K) and acetyl salicylic acid (Compound L) were used as comparative compounds.

(Method)

Left hind leg of male SD rat (one group: 3 to 5 rats) was dipped in dry ice-ethanol for 2 seconds, and after 30 minutes, 30 mg/kg of a test compound dissolved in pure water was administered to the rat and then orally administered twice a day for 6 days continuously. At the final day of the experiment, volumes of both hind legs (below ankle joint) of the rat were measured by a water substitution method and an edema ratio was calculated from the following equation. Also, an inhibition ratio of the test compound administered group was obtained by comparing the edema ratio of the group in which the test compound was not administered.

$$\text{Edema ratio (\%)} = \left[1 - \frac{\text{Left hind leg volume (treated)}}{\text{Right hind leg volume (non-treated)}}\right] \times 100$$

The present model is disclosed, for example, in Hayashi et al, "Pharmacological Studies on Niceritrol (10), The Effects on Experimental Models of Peripherally Circulatory Insufficiency", Applied Pharmacology, 24 (6): 859–864 (1982), noting particularly the section "2. Effect on an experimental frostbite model" on page 860.

(Results)

The edema ratio and inhibition ratio of edema are as shown in the following Table 10.

TABLE 10

| Compound | Edema (%) | % Inhibition of edema |
| --- | --- | --- |
| Vehicle | 44 ± 2 | — |
| A | 32 ± 8 | 27 |
| K | 48 ± 2 | −9 |
| L | 55 ± 8 | −25 |

Clinical Example

The test compound A was administered per os 100 mg/day or 200 mg/day once a day after breakfast for 6 weeks to 49 patients who are patients of arteriosclerosis obliterans or Buerger's disease wherein ischemic ulcer had been diagnosed and obliterating portion had been confirmed.

Improved degrees of respective symptoms, such as the size of ulcer, characteristics of granulation, pain at rest, frigidity and numbness of the arms and legs, were judged in principle by the following standard and evaluated comprehensively. As a result, among 40 patients, which are excluding 9 exceptional cases, "remarkable improvement" or "improvement" was seen in 25 patients (62.5%).

(1) Improved degree of a size of ulcer (size of ulcer: $\sqrt{\text{major axis} \times \text{minor axis}}$)

1. Remarkably improved: Cured or shrunk 50% or more
2. Improved: Shrunk 50 to 30%
3. Slightly improved: Shrunk 30 to 5%
4. No change: Shrunk 5 to −5%
5. Expanded: Expanded 5% or more.

(2) Improved degrees of characteristics of granulation, pain at rest, frigidity and numbness of the arms and legs 1. Remarkably improved: Disappeared or improved in serious degree of 3 ranks or more
2. Improved: Disappeared or improved in serious degree of 2 ranks or more
3. Slightly improved: improved in serious degree of 1 rank
4. No change: Not changed
5. Worsened: Worsened in serious degree of 1 rank or more.

Preparation Example (1) A mixture comprising 2.48 g of (−)-cis-2-(4-methylphenyl)- 3-hydroxy-8-trityloxymethyl-2,3-dihydro-1,5-benzothiazepin-4(5H)-one, 0.75 g of 2-(dimethylamino) ethyl chloride hydrochloride, 1.70 g of potassium carbonate and 50 ml of acetone was refluxed overnight while stirring. After the mixture was cooled, insoluble materials were removed by filtration, and the filtrate was concentrated under reduced pressure. The residual was recrystallized from a mixed solution of ethyl acetate and n-hexane to give 2.59 g of (−)-cis-2-(4-methylphenyl)-3-hydroxy-5-[2-(dimethylamino)ethyl]-8-trityloxymethyl-2,3-dihydro-1,5-benzothiazepin-4(5H)-one.

m.p.: 110° to 114° C.

$[\alpha]_D^{20}$ −83.7° (C=0.251, methanol).

(2) A mixture of 2.46 g of the compound obtained in the above (1), 9 ml of acetic anhydride and 25 ml of pyridine was stirred overnight at room temperature. The reaction mixture was poured into water with ice, and extracted with ethyl acetate. The extract was washed, dried, and concentrated under reduced pressure to give 2.72 g of (−)-cis-2-(4-methylphenyl)-3-acetoxy-5-[2-(dimethylamino)ethyl]-8-trityloxymethyl-2,3-dihydro-1,5-benzothiazepin-4(5H)-one as an oily material.

$IR^{liquid} \nu_{max}$ (cm$^{-1}$): 1745, 1680.

(3) The compound obtained in the above (2) in an amount of 2.0 g was dissolved in 20 ml of trifluoroacetic acid, followed by stirring at room temperature for 3 hours, and the mixture was concentrated under reduced pressure. To the residue were added 200 ml of saturated aqueous solution of sodium hydrogen carbonate and 100 ml of diethyl ether and the resulting mixture was stirred at room temperature for 30 minutes.

The reaction mixture was extracted with ethyl acetate, and the extract was concentrated under reduced pressure to give (−)-cis-2-(4-methylphenyl)-3-acetoxy-5-[2-(dimethylamino)ethyl]-8-hydroxymethyl-2,3-dihydro-1,5-benzothiazepin-4(5H)-one as a crude product.

The product was treated with oxalic acid, and recrystallized from a mixed solution comprising ethanol and ether to give 966 mg of (−)-cis-2-(4-methylphenyl)-3-acetoxy-5-[2-(dimethylamino)ethyl]-8-hydroxymethyl-2,3-dihydro-1,5-benzothiazepin-4(5H)-one oxalate.

m.p.: 168° to 169° C.

$[\alpha]_D^{20}$ −83.1° (C=0.201, methanol).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

We claim:

1. A method for prophylaxis or treatment of conditions responsive to improved peripheral circulation in a warm-blooded animal, comprising the step of administering to said warm-blooded animal a (−)-cis-1,5-benzothiazepine compound represented by the following formula:

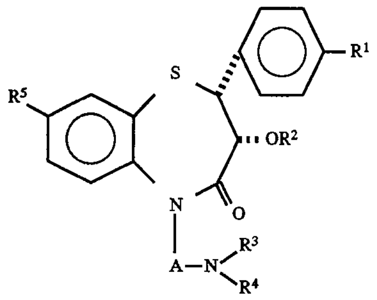

(I)

wherein $R^1$ represents lower alkyl or lower alkoxy; $R^2$ represents hydrogen or lower alkanoyl; $R^3$ represents lower alkyl; $R^4$ represents hydrogen or lower alkyl; $R^5$ represent hydrogen, lower alkyl or hydroxy lower alkyl; and A represents lower alkylene, or a pharmaceutically acceptable salt thereof, at an amount which is effective for conditions responsive to improved peripheral circulation but shows substantially no effect on vertebral arterial blood flow or blood pressure.

2. A method according to claim 1, wherein $R^1$ is lower alkyl, $R^2$ is lower alkanoyl, $R^4$ is lower alkyl, and $R^5$ is lower alkyl.

3. A method according to claim 1, wherein $R^1$ is lower alkyl having 1 to 6 carbon atoms or lower alkoxy having 1 to 6 carbon atoms, $R^2$ is hydrogen or lower alkanoyl having 2 to 6 carbon atoms, $R^3$ is lower alkyl having 1 to 6 carbon atoms, $R^4$ is hydrogen or lower alkyl having 1 to 6 carbon atoms, $R^5$ is hydrogen, lower alkyl having 1 to 6 carbon atoms or hydroxy lower alkyl having 1 to 6 carbon atoms and A is lower alkylene having 1 to 6 carbon atoms.

4. A method according to claim 2, wherein $R^1$ is lower alkyl having 1 to 6 carbon atoms, $R^2$ is lower alkanoyl having 2 to 6 carbon atoms, $R^3$ is lower alkyl having 1 to 6 carbon atoms, $R^4$ is lower alkyl having 1 to 6 carbon atoms, $R^5$ is lower alkyl having 1 to 6 carbon atoms, and A is lower alkylene having 1 to 6 carbon atoms.

5. A method according to claim 1, wherein $R^1$ is methyl, $R^2$ is acetyl, $R^3$ is methyl, $R^4$ is methyl, $R^5$ is methyl and A is ethylene.

6. A method according to claim 5, wherein said condition is chronic arterial obstruction.

7. A method according to claim 5, wherein said condition is Buerger's disease.

8. A method according to claim 5, wherein said condition is arteriosclerosis obliterans.

9. A method according to claim 5, wherein said condition is Raynaud's disease.

10. A method according to claim 1, wherein said compound ms orally administered to provide a daily dosage level of 0.1 to 300 mg/kg in said animal.

11. A method according to claim 1, wherein said compound is parenterally administered to provide a daily dosage level of 0.001 to 10 mg/kg in said animal.

* * * * *